(12) United States Patent
Shkolnikov et al.

(10) Patent No.: US 11,253,857 B2
(45) Date of Patent: Feb. 22, 2022

(54) NUCLEIC ACID SEPARATION

(71) Applicant: HEWLETT-PACKARD DEVELOPMENT COMPANY, L.P., Spring, TX (US)

(72) Inventors: Viktor Shkolnikov, Palo Alto, CA (US); Alexander Govyadinov, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 16/605,927

(22) PCT Filed: Mar. 27, 2018

(86) PCT No.: PCT/US2018/024672
§ 371 (c)(1),
(2) Date: Oct. 17, 2019

(87) PCT Pub. No.: WO2019/190490
PCT Pub. Date: Oct. 3, 2019

(65) Prior Publication Data
US 2021/0121883 A1 Apr. 29, 2021

(51) Int. Cl.
*B01L 3/00* (2006.01)
*B01L 7/00* (2006.01)
(52) U.S. Cl.
CPC ......... *B01L 3/502761* (2013.01); *B01L 7/525* (2013.01); *B01L 2200/0652* (2013.01);
(Continued)
(58) Field of Classification Search
CPC ......... B01L 2200/0652; B01L 2200/16; B01L 2300/0864; B01L 2300/0867;
(Continued)

(56) References Cited

U.S. PATENT DOCUMENTS

| 9,132,426 B2 | 9/2015 | Prakash |
| 9,562,837 B2 | 2/2017 | Link |

(Continued)

FOREIGN PATENT DOCUMENTS

| EP | 2664666 B1 | 6/2017 |
| WO | WO2006108101 A2 | 10/2006 |

(Continued)

OTHER PUBLICATIONS

Fan, Z. Hugh, et al., Dynamic DNA Hybridization on a Chip, Sep. 28, 1999, Analytical Chemistry.

(Continued)

*Primary Examiner* — Jennifer Wecker
(74) *Attorney, Agent, or Firm* — Middleton Reutlinger

(57) ABSTRACT

An example system includes an input channel to flow nucleic segments therethrough, a mixing portion coupled to the input channel, a separation chamber in fluid communication with the second end of the input channel, at least two output channels coupled to the chamber, and an integrated pump to facilitate flow through the separation chamber. The mixing portion is to include at least two different categories of beads having different sizes from each other and having a probe to attach to a corresponding nucleic acid segment. The separation chamber has a passive separation structure including an array of columns spaced apart to facilitate separation of the different categories of beads and attached corresponding nucleic acid segment into at least two flow paths based on a size of the category of the beads. Each output channel is to receive separated categories of beads and attached nucleic acid segments.

15 Claims, 3 Drawing Sheets

(52) U.S. Cl.
CPC ... *B01L 2200/16* (2013.01); *B01L 2300/0867* (2013.01); *B01L 2400/021* (2013.01); *B01L 2400/0439* (2013.01)

(58) Field of Classification Search
CPC ....... B01L 2400/021; B01L 2400/0439; B01L 2400/0487; B01L 3/502753; B01L 3/502761; B01L 7/525; C12Q 1/6806
See application file for complete search history.

(56) References Cited

U.S. PATENT DOCUMENTS

| | | |
|---|---|---|
| 2004/0144651 A1 | 7/2004 | Huang et al. |
| 2008/0113358 A1 | 5/2008 | Kapur et al. |
| 2009/0162929 A1 | 6/2009 | Ikeda |
| 2011/0014605 A1 | 1/2011 | Stone |
| 2014/0377145 A1* | 12/2014 | Govyadinov ....... B01F 13/0059 422/505 |
| 2018/0056294 A1* | 3/2018 | Di Carlo .......... G01N 33/54333 |
| 2018/0080060 A1* | 3/2018 | Gifford ............. G01N 15/1056 |

FOREIGN PATENT DOCUMENTS

| | | |
|---|---|---|
| WO | WO2017035262 A1 | 3/2017 |
| WO | WO2017117666 A1 | 7/2017 |

OTHER PUBLICATIONS

Wu, Jinbo, et al., Extraction, amplification and detection of DNA, Dec. 20, 2013, Microchim Acta.

* cited by examiner

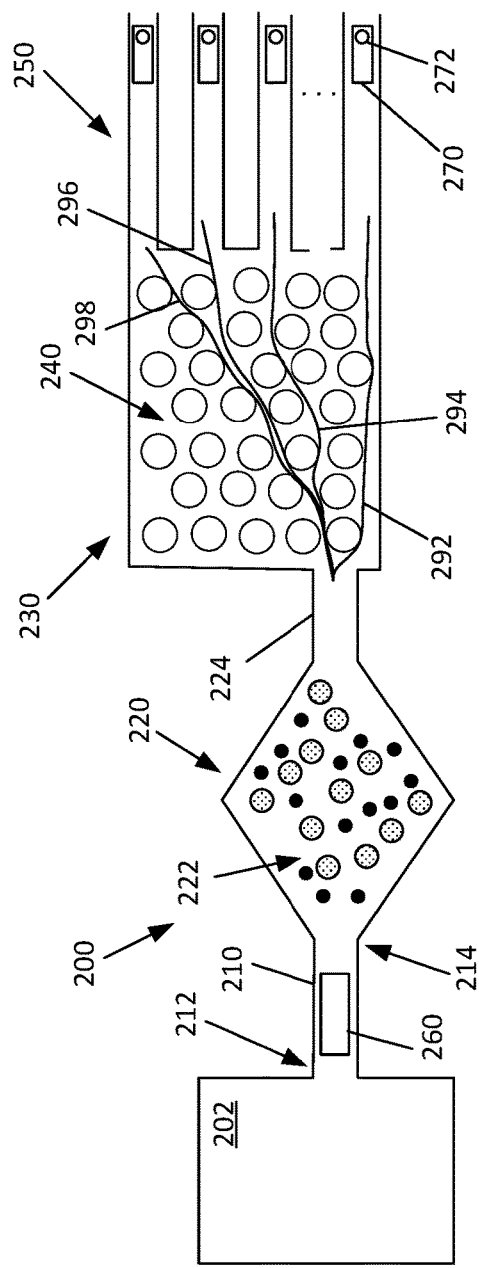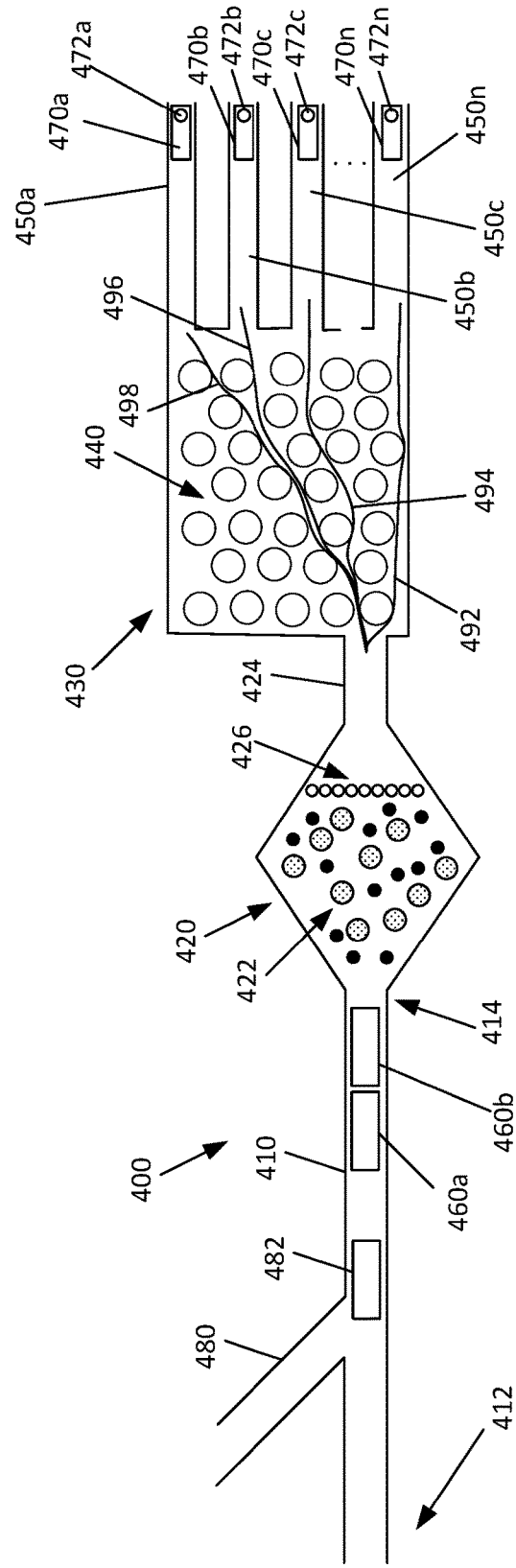

NUCLEIC ACID SEPARATION

BACKGROUND

Analysis of genetic information has become pervasive in many areas. For example, analysis of DNA, or Deoxyribonucleic acid, is commonly used in crime solving, genetic profiling, etc. In many cases, DNA is obtained from various sources, such as blood cells, and analyzed for purposes such as, for example, matching with a crime suspect or identification of a gene associated with a disease.

BRIEF DESCRIPTION OF THE DRAWINGS

For a more complete understanding of various examples, reference is now made to the following description taken in connection with the accompanying drawings in which:

FIG. 3 illustrates separation of nucleic acid segments in the example system of FIG. 2;

FIG. 4 illustrates another example system for separation of nucleic acid segments;

DETAILED DESCRIPTION

As noted above, genetic material is commonly used in a variety of fields. In some examples, analysis of the genetic material may be performed with the use of microfluidic devices. Microfluidic devices may be provided to flow fluids through narrow channels to, for example, reaction chambers. In various examples, the fluids may include any number of particles within a flow. A reaction chamber or another output of the channels may use the particles in a separated or concentrated condition. Accordingly, the various particles in a flow are separated (e.g., sorted or categorized) for use within the microfluidic device or for output from the microfluidic device. In other examples, the various particles may be purified, or concentrated.

In order to separate the particles, some devices use a system of sensors and valves to open a corresponding channel to direct a particle into an appropriate channel. Such sensors and valves typically result in slowing of the flow upstream of the valve. Further, such sensors and valves have the potential to fail, resulting in failure of sorting in all output channels.

Further, categorizing or flow of particles may be facilitated with the use of external pumps. External pumps (e.g., syringe pumps or capillary pumps) may increase complexity and expense by requiring a pump to be outside the lab-on-a-chip, for example.

Various examples described herein relate to separation of DNA (or nucleic acid) segments in, for example, a microfluidic device. A flow of DNA segments is combined with a stream containing different sized beads. The beads are of different sizes, each size containing a probe to attract and attach to a specific DNA segment. Thus, each type of DNA segment attaches to a corresponding sized bead. The beads are then sorted by directing beads through a chamber of passive separation structures. The passive separation structure may include columns, or posts, that are spaced apart in a manner which directs particles in the flow along different paths based on the size of the particles. Thus, the different sized beads, each with a corresponding DNA segment is directed to a different flow path. The device includes at least one integrated pump, such as an inertial pump, in the input channel or an output channel to facilitate flow of the beads and DNA segments. In various examples, the integrated pumps are thermal inkjet resistors.

Figure 1:
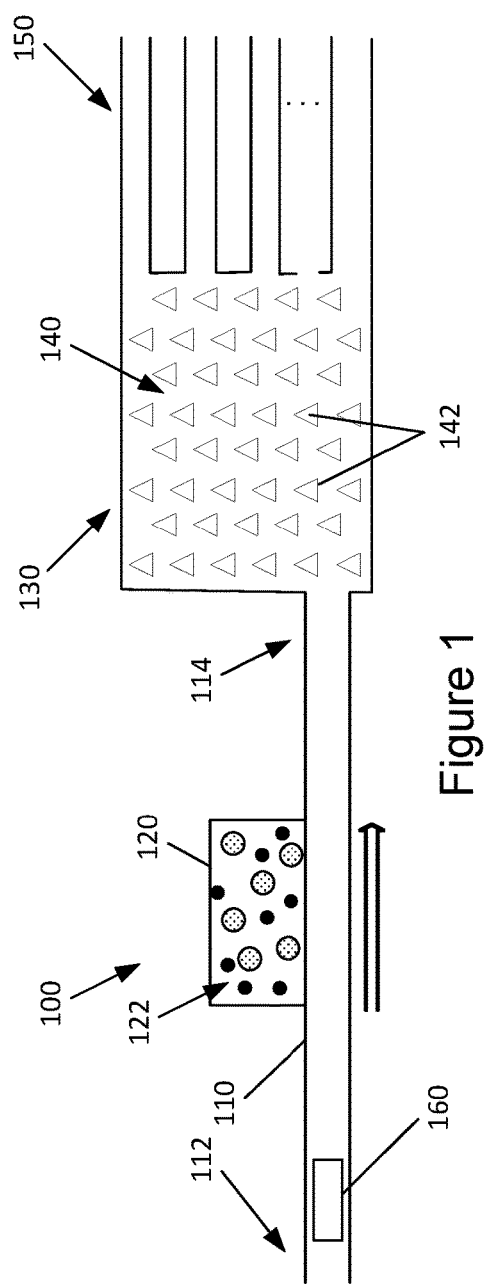
FIG. 1 illustrates an example system for separation of nucleic acid segments.

Referring now to the Figures, FIG. 1 illustrates an example system for separation of nucleic acid segments. The example system may be any of a variety of devices, such as microfluidic devices, lab-on-a-chip, or micro total analytical systems, for example. In the example of FIG. 1, the example system 100 includes an input channel 110 with a first end 112 and a second end 114. The input channel 110 may receive particles, such as nucleic acid fragments, therein through the first end 112. An arrow in the input channel 110 illustrated in FIG. 1 indicates the direction of flow of the particles. In various examples, the input channel 110 may be a long and/or narrow channel.

In various examples, the example system 100 is a microfluidic device, and the input channel 110 is a microfluidic channel. In one example, the input channel 110 has a cross-sectional width of between about 10 μm and about 500 μm. Various examples of the system 100 may be formed by performing various microfabrication and/or micromachining processes on a substrate to form and/or connect structures and/or components. The substrate may comprise a silicon based wafer or other such similar materials used for microfabricated devices (e.g., glass, gallium arsenide, plastics, etc.). Examples may comprise microfluidic channels, fluid actuators, and/or volumetric chambers. Microfluidic channels and/or chambers may be formed by performing etching, microfabrication processes (e.g., photolithography), or micromachining processes in a substrate. Accordingly, microfluidic channels and/or chambers may be defined by surface or bulk micromachining and fabricated in the substrate of a microfluidic device. Other examples of microfluidic device fabrication may include, without limitation, injection molding or hot embossing, for example. In some implementations, microfluidic channels and/or chambers may be formed by an overall package, wherein multiple connected package components that combine to form or define the microfluidic channel and/or chamber.

In various examples, a stream of nucleic acid fragments flowing through the input channel 110 may include two, three, or more different fragments or categories of fragments. For example, the different categories of fragments may be different segments of a genetic sequence.

The example system 100 further includes a mixing portion 120 that is coupled to (e.g., in fluid communication with) the input channel 110. The mixing portion 120 is provided with a reservoir of at least two different categories of beads. Each category of beads has a different size than the other categories of beads provided in the mixing portion 120. The difference in the sizes of the categories of beads is sufficient to allow separation in the separation chamber 130 described below. Each category of beads is provided with a probe to attach to a specific nucleic acid fragment, or a specific category of nucleic acid fragments.

In the example of FIG. 1, the example system 100 includes a separation chamber 130. The separation chamber 130 is in fluid communication with the second end 114 of the input channel 110. Thus, the separation chamber 130 may receive a flow of nucleic acid fragments (e.g., fragments received through the first end 112 of the input channel 110) attached to a corresponding bead (e.g., bead from the mixing portion 120) flowing through the second end 114 of the input channel 110. In various examples, the separation chamber 130 includes a passive separation structure 140 to separate particles in a flow based on the size of the particles. The passive separation structure 140 of the example system 100 includes an array of columns 142, or posts, that are arranged to facilitate separation of particles in the flow based on the size of the particles. For example, the columns 142 may be arranged in accordance with principles of deterministic lateral displacement (DLD), which is described below in greater detail with reference to FIG. 2.

In the illustration of FIG. 1, the flow of nucleic acid fragments attached to beads enters the separation chamber 130 from the left side. As the particles flow through the separation chamber 130, the array of columns 142 causes the particles to separate according to size. In this regard, the example system 100 includes at least two output channels 150. Each output channel is in fluid communication with the separation chamber 130 and positioned to receive separated particles. Thus, each output channel 150 is positioned to receive nucleic acid fragments attached to beads of a certain size or range of sizes.

In various examples, the passive separation structure 140 separates the particles in the flow into at least two flow paths based on a size of the particles. As noted above, each output channel 150 is positioned to receive particles of a certain size or range of sizes. In this regard, each flow path is directed to one of the output channels 150.

The example system 100 of FIG. 1 is provided with an integrated pump 160 to facilitate flow of particles through the separation chamber 130. While the example system 100 of FIG. 1 is provided with the integrated pump 160 in the input channel 110, in various examples, the integrated pump 160 may be positioned within the input channel 110, an output channel 150 or a combination thereof. Thus, the integrated pump 160 may be a push pump provided in the input channel 110, as shown in FIG. 1, or a pull pump provided in an output channel 150.

In the example in which the example system 100 is a microfluidic device, each integrated pump 160 may be an inertial pump. As used herein, an inertial pump corresponds to a fluid actuator and related components disposed in an asymmetric position in a microfluidic channel, where an asymmetric position of the fluid actuator corresponds to the fluid actuator being positioned less distance from a first end of a microfluidic channel as compared to a distance to a second end of the microfluidic channel. Accordingly, in some examples, a fluid actuator of an inertial pump is not positioned at a mid-point of a microfluidic channel. The asymmetric positioning of the fluid actuator in the microfluidic channel facilitates an asymmetric response in fluid proximate the fluid actuator that results in fluid displacement when the fluid actuator is actuated. Repeated actuation of the fluid actuator causes a pulse-like flow of fluid through the microfluidic channel.

In some examples, an inertial pump includes a thermal actuator having a heating element (e.g., a thermal resistor) that may be heated to cause a bubble to form in a fluid proximate the heating element. In such examples, a surface of a heating element (having a surface area) may be proximate to a surface of a microfluidic channel in which the heating element is disposed such that fluid in the microfluidic channel may thermally interact with the heating element. In some examples, the heating element may comprise a thermal resistor with at least one passivation layer disposed on a heating surface such that fluid to be heated may contact a topmost surface of the at least one passivation layer. Formation and subsequent collapse of such bubble may generate unidirectional flow of the fluid. As will be appreciated, asymmetries of the expansion-collapse cycle for a bubble may generate such flow for fluid pumping, where such pumping may be referred to as "inertial pumping." In other examples, a fluid actuator corresponding to an inertial pump may comprise a membrane (such as a piezoelectric membrane) that may generate compressive and tensile fluid displacements to thereby cause fluid flow.

Figure 2:
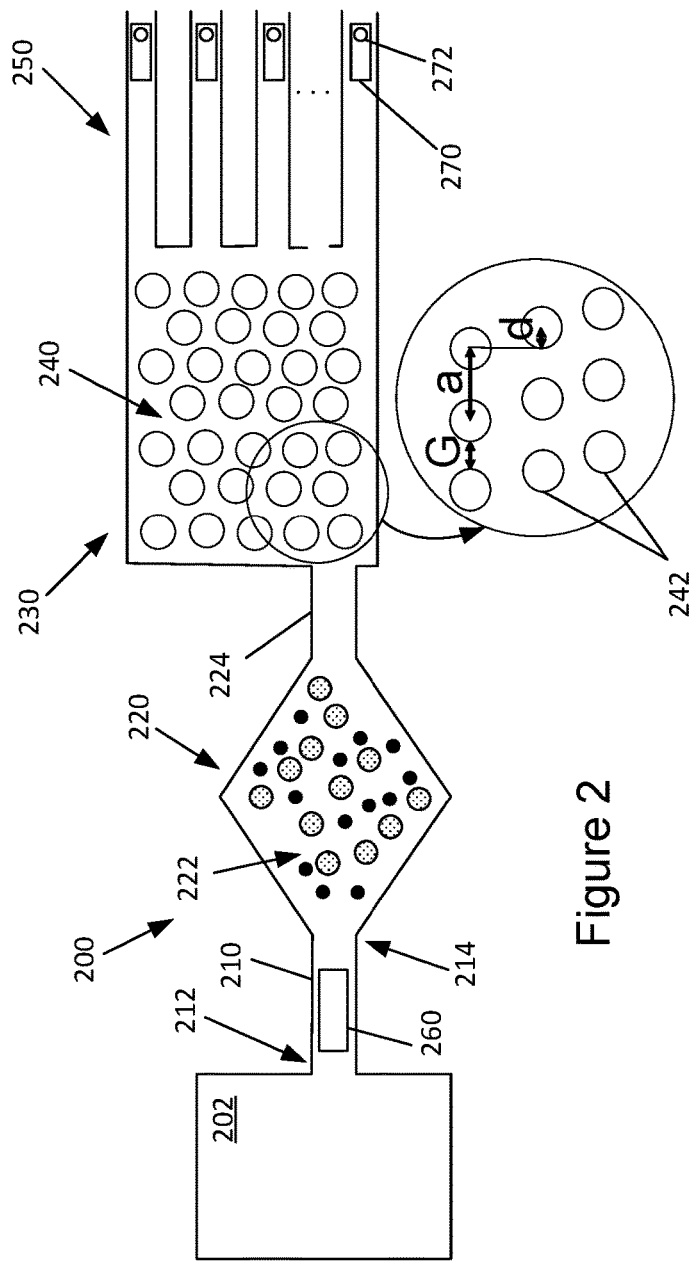
FIG. 2 illustrates another example system for separation of nucleic acid segments.

Referring now to FIG. 2, another example system for separation of nucleic acid segments is illustrated. The example system 200 of FIG. 2 is similar to the example system 100 of FIG. 1 and includes an input channel 210, a mixing portion 220, a separation chamber 230, and a set of output channels 250. Similar to the example system 100 of FIG. 1, the input channel 210 has a first end 212 and a second end 214. The mixing portion 220 is provided with a reservoir of at least two different categories of beads 222, each category of beads having a different size than the other categories of beads. The separation chamber 230 is in fluid communication with the mixing chamber 220 through a focusing channel 224. The separation chamber 230 includes a passive separation structure 240 which includes an array of columns 242 arranged to facilitate separation of particles (e.g., nucleic acid segments attached to corresponding beads) in the flow based on the size of the particles. The flow of particles is separated into different flow paths based on the size of the particles in the flow.

The example system 200 of FIG. 2 is provided with an integrated pump 260 in the input channel 210. In order to reduce pulsing in the separation chamber 230 due to operation of the integrated pump 260, the mixing chamber 220 of the example system 200 works as a dampening chamber which allows for a more steady flow of particles into the separation chamber 230 through the focusing channel 224. In the example system 200 of FIG. 2, a sample reservoir 202 is provided for supplying a flow of nucleic segment fragments to the input channel 210. In various examples, the integrated pump 260 may draw fragments from the sample reservoir 202 for flow through the input channel 210, the mixing portion 220 and the separation chamber 230. In various examples, the sample reservoir 202 may be replaceable or refillable.

In addition to the integrated pump 260 in the input channel, each output channel 250 of the example system 200 is provided with an integrated pump 270. The integrated pumps 270 in the output channels 250 are coupled to nozzles 272 to allow ejection of the separated nucleic acid fragments, for example. The nozzles 272 may allow the separated fragments to be selectively drawn or ejected as desired. In one example, the integrated pumps 270 in the output channels 250 include a piezo element, forming a piezoelectric micro pump. In various examples, the piezo element and the nozzle 272 form a drop ejector to allow the separated particles to be drawn or dropped from the output channel 250. In this regard, a drop ejector allows control of flow through an individual output channel 250. In other examples, the integrated pump includes an inertial pump or a drop ejection nozzle actuated by thermal inkjet resistor (TIJ).

As noted above, the passive separation structure 240 includes an array of columns 242 that may be arranged in accordance with DLD principles. DLD uses a specific arrangement of obstacles, such as columns 242, to control the path, or trajectory, of particles to separate particles larger than a critical diameter from those smaller than the critical diameter through collisions with the obstacles. In a flow, when a particle is larger than the critical diameter, its center is positioned such that collision with an obstacle causes the larger particle to flow to one side of the obstacle. Meanwhile, collision of objects smaller than the critical diameter the same obstacle causes the smaller particle to flow to the other side of the obstacle.

In various examples, the columns 242 may be formed with any of a variety of shapes, or cross-sectional shape. For example, the columns 242 may be formed as circular, triangular or any polygonal shape, for example. Further, the array of columns 242 may be formed with the columns 242 have a particular size (e.g., cross-sectional diameter), a column spacing (G) and a column pitch (d/a). The array of columns may be formed to separate particles based on a critical diameter, which may be calculated as $2*\alpha*G*pitch$, where $\alpha$ is a non-dimensional correction factor determined as $sqrt(a/3d)$. In one example, the array of columns 242 is formed to separate particles of 0.75 μm. In this example, the columns 242 may be formed as circular cylinders having a cross-sectional diameter of 5 μm, a pillar spacing (G) of 5 μm and a pitch (d/a) of 0.01. In this arrangement, particles larger than 0.75 μm are separated from particles smaller than 0.75 μm.

In various examples, the separation chamber 230 may be divided into zones to further separate particles. For example, in a first zone, the particles may be divided based on a critical diameter of 0.75 μm, as described above. In a downstream zone, the particles larger than 0.75 μm maybe further separated with a critical diameter of 1.00 μm. Thus, three paths may be formed with a first path for particles smaller than 0.75 μm, a second path for particles larger than 0.75 μm but smaller than 1.00 μm, and a third path for particles larger than 1.00 μm. Of course, the particles may be separated into as many size categories as desired or as may be accommodated by the size of the separation chamber.

In this regard, FIG. 3 illustrates separation of particles in the example system 200 of FIG. 2. FIG. 3 illustrates separation of flow into four paths. As noted above, any practical number of paths may be formed in the separation chamber 230. In the example of FIG. 3, the passive separation structure 240 results in particles in four size categories being directed along a corresponding path 292, 294, 296, 298. Each of the paths 292, 294, 296, 298 corresponds to one of the output channels 250.

In various examples described and illustrated herein, an inlet (e.g., the focusing channel 224) of the flow of particles into the separation chamber 230 is positioned to provide a flow to a particular region of the separation chamber 230. For example, FIGS. 2 and 3 illustrate the focusing channel 224 being in fluid communication with a lower left portion of the separation chamber 230. It will be understood that, in various examples, an input to the separation chamber 230, such as the focusing channel 224 or the input channel 110 of FIG. 1, may be positioned to interface with other regions of the separation chamber 230. For example, the focusing channel 224 may be coupled to a central or upper left portion of the separation chamber 230. In this regard, the passive separation structure 240 may form paths 292, 294, 298, 298 from the specific input region to the various output channels 250.

Referring now to FIG. 4, another example system 400 for separation of nucleic acid segments is illustrated. The example system 400 of FIG. 4 is similar to the example system 200 of FIG. 2. In this regard, the example system 400 includes an input channel 410 with a first end 412 and a second end 414, a mixing portion 420, a separation chamber 430 with a passive separation structure 440 formed with an array of columns 442, and a set of output channels 450.

The mixing portion 420 of the example system 400 serves as a dampening chamber and is in fluid communication with the separation chamber 430 through a focusing channel 424. The example system 400 of FIG. 4 is provided with integrated pumps 460a, 460b in the input channel 410, as well as integrated pumps 470a-n in the output channels 440a-n. As noted above, each integrated pump 470a-n in the output channels 450a-n is coupled to a nozzle 472a-n.

The example system 400 of FIG. 4 is further provided with a reagent input channel 480. The reagent input channel 480 is in fluid communication with input channel 410. In various cases, the flow into the input channel 410 through the first end 412 may include cells, such as blood cells. The reagent input channel 480 may be used to mix a reagent, such as a lysing agent, with the flow of cells in the input channel 410. In this regard, a mixing pump 482 may be provided to facilitate or control the mixing of the cells with lysing agent in the input channel 410. The mixing pump 482 may be similar to the pumps 460a,b and 470a-n and may be an integrated pump (e.g., an inertial pump). The lysing agent may cause biological material, such as nucleic acid segments, from the cell. The nucleic acid segments may then be flowed into the mixing portion 420 for attachment with corresponding beads 422.

As noted above, in the example system 400 of FIG. 4, the mixing portion 420 serves as a dampening chamber. In this regard, the mixing portion 420 is provided with dampening features 426 to facilitate reduction of pulsing in the separation chamber 430. In various example, the features may include an array of orifices, an elastic membrane or other such features. In one example, the dampening features 426 are orifices that are round, rectangular or other geometric shape.

Figure 5:
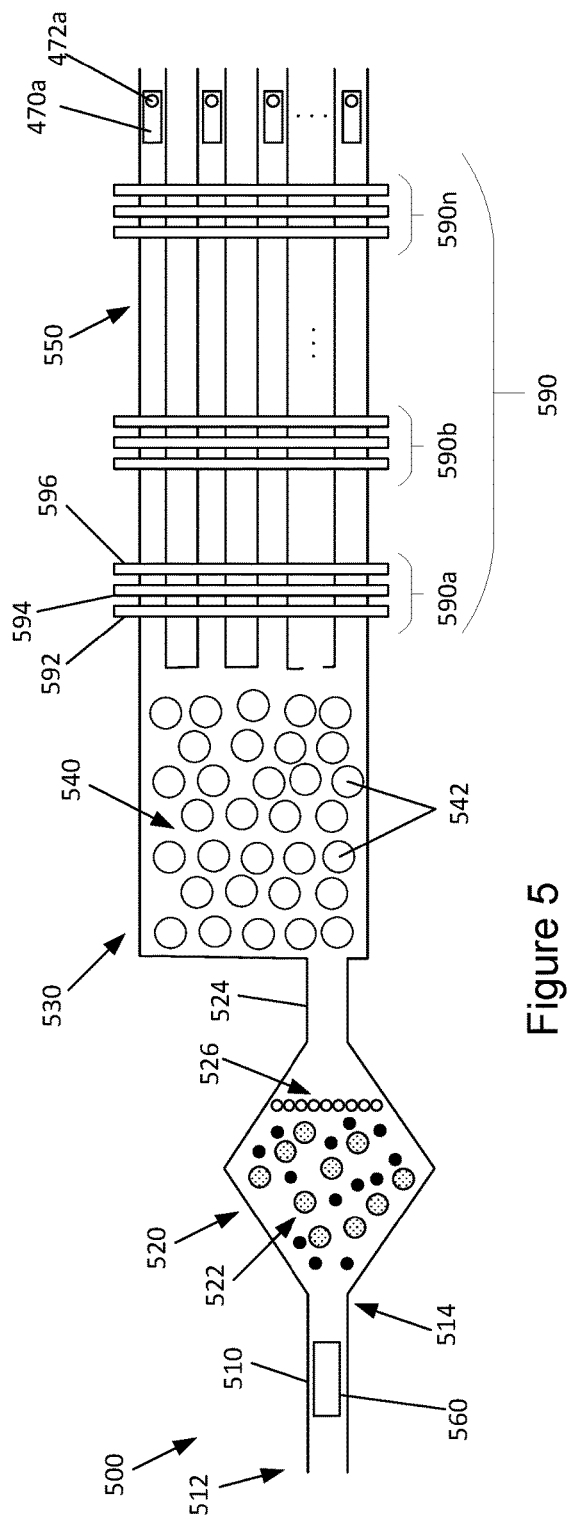
FIG. 5 illustrates another example system for separation of nucleic acid segments.

Referring now to FIG. 5, another example system 500 for separation of nucleic acid segments is illustrated. The example system 500 of FIG. 5 is similar to the example system 200 of FIG. 2. In this regard, the example system 500 includes an input channel 510 with a first end 512 and a second end 514, a mixing portion 520, a separation chamber 530 with a passive separation structure 540 formed with an array of columns 542, a set of output channels 550, and an integrated pump 560 in the input channel 510 and integrated pumps 570a-n and corresponding nozzles 572a-n in the output channels 550.

Similar to the example system 400 of FIG. 4, the mixing portion 520 of the example system 500 serves as a dampening chamber and is in fluid communication with the separation chamber 530 through a focusing channel 524. In this regard, the mixing portion 520 includes dampening features 526.

In various examples, the separation chamber 530 provides separated nucleic acid fragments in each of the output channels 550. In the example system 500 of FIG. 5, a nucleic acid segment amplification portion 590 is provided in fluid communication with at least one output channel. In this regard, the amplification portion 590 in the example of FIG. 5 is integrally formed with the output channels 550.

The amplification portion 590 is provided to amplify biological material from the lysed cells, such as the separated nucleic acid segments. In this regard, the amplification portion 590 is positioned to receive biological material in the output channels 550 and to provide the amplified biological material to the pumps 570a-n and nozzles 572a-n, for example, for analysis or detection.

In the example system 500 of FIG. 5, the nucleic acid segment amplification portion 590 includes a series of thermal zones 590a-n to cycle temperature as the nucleic acid segments flow through the output channel 550. In this regard, the separated nucleic acid segments in each output channel 550a-n may be processed through a polymerase chain reaction (PCR) for amplification. In one example, each thermal zone 590a-n cycles the separated nucleic acid segments through a series of temperature regions. In the example illustrated in FIG. 5, each thermal zone 590a-c includes three temperature regions 592, 594, 596, the temperature in each temperature region 592, 594, 596 being selected for amplification. In one example, the three temperature regions 592, 594, 596 have temperatures set at 95° C., 55° C. and 72° C., respectively.

Figure 6:
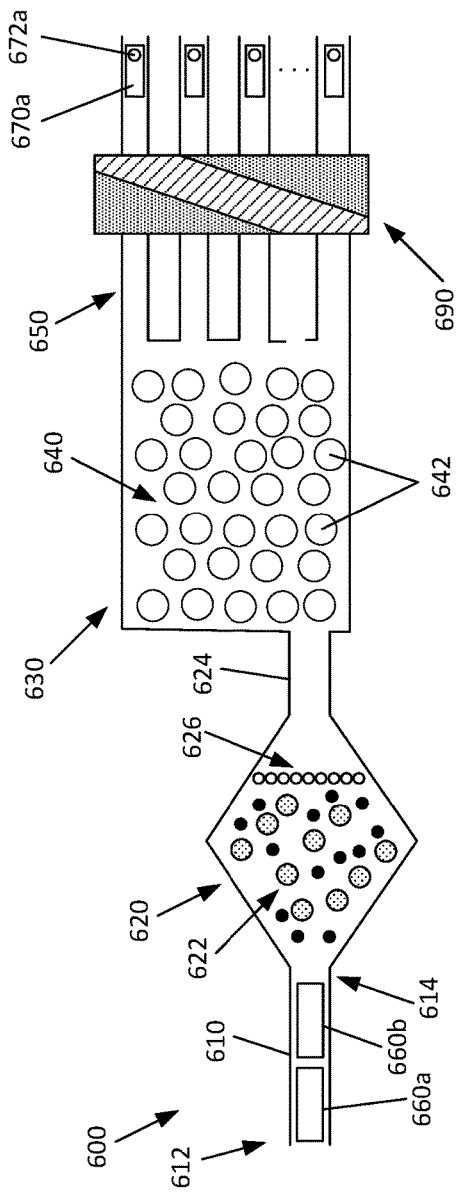
FIG. 6 illustrates another example system for separation of nucleic acid segments.

Referring now to FIG. 6, another example system 600 for separation of nucleic acid segments is illustrated. The example system 600 of FIG. 6 is similar to the example system 500 of FIG. 5. In this regard, the example system 600 includes an input channel 610 with a first end 612 and a second end 614, a mixing portion 620, a separation chamber 630 with a passive separation structure 640 formed with an array of columns 642, a set of output channels 650, and integrated pumps 660a, 660b in the input channel 610 and integrated pumps 670a-n and corresponding nozzles 672a-n in the output channels 650.

Similar to the example system 500 of FIG. 5, the mixing portion 620 of the example system 600 serves as a dampening chamber and is in fluid communication with the separation chamber 630 through a focusing channel 624. In this regard, the mixing portion 620 includes dampening features 626.

The example system 600 of FIG. 6 further includes an amplification portion 690 in fluid communication with at least one output channel 650. The amplification portion 690 of the example system 600 is a zone s provided to amplify biological material from the lysed cells, such as the separated nucleic acid segments. In the example system 600 of FIG. 6, the amplification portion 690 includes a thermocycling zone. The temperature in the thermocycling zone is actively cycled through various temperatures to facilitate amplification of the nucleic acid segments. The temperature profile in the thermocycling zone may be selected for particular applications. In one example, the temperature profile in the thermocycling zone includes a denaturation step with the temperature at about 95 C followed by a primer annealing step at about 65 C and a primer extension step at about 73 C. Material in the thermocycling zone may be exposed to numerous cycles of the temperature profile. In one example, the material may be exposed to between about 25 and about 50 cycles of the temperature profile, with each step in each cycle lasting between about 1 millisecond and about 20 minutes. In one example, each step in each cycle lasts about 2 minutes.

Thus, the example systems described above provide an efficient, cost-effective and user-friendly system for separation of nucleic acid segments. Various examples include an integrated system which includes pumping and separation of the segments, resulting in significant advantages, such as elimination of transfer of particles from one system to another and elimination of additional external components such as pumps.

The foregoing description of various examples has been presented for purposes of illustration and description. The foregoing description is not intended to be exhaustive or limiting to the examples disclosed, and modifications and variations are possible in light of the above teachings or may be acquired from practice of various examples. The examples discussed herein were chosen and described in order to explain the principles and the nature of various examples of the present disclosure and its practical application to enable one skilled in the art to utilize the present disclosure in various examples and with various modifications as are suited to the particular use contemplated. The features of the examples described herein may be combined in all possible combinations of methods, apparatus, modules, systems, and computer program products.

It is also noted herein that while the above describes examples, these descriptions should not be viewed in a limiting sense. Rather, there are several variations and modifications which may be made without departing from the scope as defined in the appended claims.

What is claimed is:

1. A system, comprising:
   an input channel having a first end and a second end to flow nucleic segments therethrough;
   a mixing portion coupled to the input channel, the mixing portion to include at least two different categories of beads, the at least two different categories of beads having different sizes from each other, each category of beads having a probe to attach to a corresponding nucleic acid segment;
   a separation chamber in fluid communication with the second end of the input channel, the separation chamber having a passive separation structure, the passive separation structure including an array of columns spaced apart and configured to facilitate separation of the at least two different categories of beads and attached corresponding nucleic acid segment into at least two flow paths based on a size of the category of the beads;
   at least two output channels, each output channel coupled to the separation chamber to receive separated categories of beads and attached nucleic acid segments; and
   an integrated pump configured to facilitate flow through the separation chamber, the integrated pump being disposed entirely within an inside of at least one of the input channel or one of the at least two output channels.

2. The system of claim 1, wherein the array of columns is arranged to deterministically direct a particle in a flow colliding with the array of columns to a first side if the particle in the flow is smaller than a critical diameter and to a second side if the particle in the flow is larger than the critical diameter.

3. The system of claim 1, wherein the input channel and each output channel are microfluidic channels.

4. The system of claim 3, wherein the integrated pump is an inertial pump.

5. The system of claim 3, wherein the integrated pump includes a thermal inkjet resistor or a piezo element.

6. The system of claim 1, wherein the mixing portion is a chamber positioned between the first end of the input channel and the separation chamber.

7. The system of claim 6, further comprising:
   a reagent input channel in fluid communication with the input channel, wherein flow from the reagent input channel is to mix with flow of cells in the input channel, the flow from the reagent input channel including a lysing agent to lyse cells in the input channel to release the nucleic acid segments in the cells.

8. The system of claim 1, further comprising:
   a nucleic acid segment amplification portion in fluid communication with at least one output channel.

9. The system of claim 8, wherein the nucleic acid segment amplification portion includes a series of thermal zones to cycle temperature as the nucleic acid segments flow through the output channel.

10. The system of claim 9, wherein the nucleic acid segment amplification portion includes a thermocycling zone, a temperature in the thermocycling zone cycling to facilitate amplification of the nucleic acid segments.

11. A system, comprising:
an input channel to flow cells therethrough;
a cell lysing portion to mix a lysing agent with the cells, the lysing agent to release nucleic acid segments from the cells;
a mixing portion to include at least two different categories of beads, the at least two different categories of beads having different sizes from each other, each category of beads having a probe to attach to a corresponding nucleic acid segment;
a separation chamber in fluid communication with the input channel, the separation chamber including an array of columns spaced apart and configured to facilitate separation of the at least two different categories of beads and attached corresponding nucleic acid segment into at least two flow paths based on a size of the category of beads;
at least two output channels, each output channel coupled to the separation chamber to receive separated categories of beads and attached nucleic acid segments; and
an integrated pump configured to facilitate flow through the separation chamber, said integrated pump disposed entirely within an inside of at least one of the input channel or one of the at least two output channels.

12. The system of claim 11, wherein the cell lysing portion includes a reagent input channel in fluid communication with the input channel.

13. The system of claim 11, further comprising:
a nucleic acid segment amplification portion in fluid communication with at least one output channel.

14. A system, comprising:
an input channel to flow nucleic acid segments therethrough;
a mixing portion to include at least two different categories of beads, the at least two different categories of beads having different sizes from each other, each category of beads having a probe to attach to a corresponding nucleic acid segment;
a separation chamber in fluid communication with the input channel, the separation chamber including an array of columns spaced apart and configured to facilitate separation of the at least two different categories of beads and attached corresponding nucleic acid segment into at least two flow paths based on a size of the category of beads;
at least two output channels, each output channel coupled to the separation chamber to receive separated categories of beads and attached nucleic acid segments;
an integrated pump configured to facilitate flow through the separation chamber, said integrated pump disposed entirely within an inside of at least one of the input channel or one of the at least two output channels; and
a nucleic acid segment amplification portion in fluid communication with at least one output channel.

15. The system of claim 14, wherein the integrated pump includes inertial pump or a drop ejection nozzle actuated by a thermal inkjet resistor or a piezo element.

* * * * *